United States Patent
Diamond et al.

[11] Patent Number: 6,142,957
[45] Date of Patent: Nov. 7, 2000

[54] MULTIPLE BIOPSY SAMPLING DEVICE

[75] Inventors: Bruce H. Diamond, Brookline; Donald E. Robinson, Hopkinton; Alyssa J. Dassa, Chestnut Hill; Charles Warich, Milford, all of Mass.

[73] Assignee: Boston Scientific Corporation, Watertown, Mass.

[21] Appl. No.: 08/789,949

[22] Filed: Jan. 27, 1997

Related U.S. Application Data

[63] Continuation of application No. 08/597,878, Feb. 7, 1996, abandoned, which is a continuation of application No. 08/124,272, Sep. 20, 1993, abandoned.

[51] Int. Cl.$^7$ .................................................. A61B 5/00
[52] U.S. Cl. .................................................. 600/567
[58] Field of Search ........................... 600/564–567; 606/167, 170

[56] References Cited

U.S. PATENT DOCUMENTS

| | | |
|---|---|---|
| 612,569 | 10/1898 | Moscrop . |
| 668,647 | 2/1901 | Jaenicke . |
| 1,162,901 | 12/1915 | Cantey . |
| 1,606,497 | 11/1926 | Berger . |
| 1,867,624 | 7/1932 | Hoffman . |
| 1,891,054 | 12/1932 | Pitman . |
| 2,426,535 | 8/1947 | Turkel . |
| 2,493,979 | 1/1950 | Kudd . |
| 2,496,111 | 1/1950 | Turkel . |
| 2,749,909 | 6/1956 | Ullery et al. ............................. 128/2 |
| 2,850,007 | 9/1958 | Lingley .................................. 128/754 |
| 3,001,522 | 9/1961 | Silverman . |
| 3,147,749 | 9/1964 | Marsh .................................... 128/751 |
| 3,175,554 | 3/1965 | Stewart . |
| 3,181,533 | 5/1965 | Heath . |
| 3,342,175 | 9/1967 | Bulloch . |
| 3,477,423 | 11/1969 | Griffith ................................. 128/2 |
| 3,590,808 | 7/1971 | Muller .................................. 128/2 B |
| 3,606,878 | 9/1971 | Kellogg, Jr. ........................... 128/2 B |
| 3,683,892 | 8/1972 | Harris ................................... 128/2 |
| 3,692,020 | 9/1972 | Schied ................................... 128/2 |
| 3,732,858 | 5/1973 | Banko ................................... 128/2 |
| 3,882,849 | 5/1975 | Jamshidi ............................... 128/2 |
| 3,903,892 | 9/1975 | Komiya ................................. 128/303 |

(List continued on next page.)

FOREIGN PATENT DOCUMENTS

| | | |
|---|---|---|
| 0 119 405 | 9/1984 | European Pat. Off. . |
| 0 279 358 | 8/1988 | European Pat. Off. . |
| 1378088 | 10/1964 | France . |
| 1069398 | 5/1967 | United Kingdom . |
| 1215439 | 12/1970 | United Kingdom . |
| WO93/04630 | 3/1993 | WIPO . |

OTHER PUBLICATIONS

Radial Jaw Single–Use Biopsy Forceps, Boston Scientific Corporation, 1993.
Grossman, "Gastrointestinal Endoscopy", Clinical Symposia, vol. 32, No. 3, 1980.

*Primary Examiner*—Max Hindenburg
*Attorney, Agent, or Firm*—Finnegan, Henderson, Farabow, Garrett & Dunner, L.L.P.

[57] ABSTRACT

In an aspect, the invention relates to an instrument for obtaining tissue samples from a site deep within the body. The instrument has an elongated proximal portion that is constructed to follow a long, torturous path to the site and has a distal end constructed to sever and remove a tissue sample from the body, including tissue specimens, polyps or the like. The improvement includes that the instrument is constructed to take multiple biopsy samples without being withdrawn from the body. The instrument includes a tissue sample retractor. The retractor is axially movable between an extended tissue-engaging position and a retracted position. There is an open passage into which the retractor moves when moving from the extended to the retracted position. The retractor has a distal end portion constructed to engage tissue and apply axial transporting force thereto while moving from the extended to the retracted position. The retractor is constructed to be advanced and retracted repeatedly to accumulate a series of samples in the instrument.

32 Claims, 16 Drawing Sheets

U.S. PATENT DOCUMENTS

| | | | |
|---|---|---|---|
| 3,924,608 | 12/1975 | Mitsui | 128/751 |
| 3,955,578 | 5/1976 | Chamness et al. | 128/303 |
| 3,989,033 | 11/1976 | Halpern et al. | 128/2 |
| 3,989,049 | 11/1976 | Yoon | 128/326 |
| 3,996,935 | 12/1976 | Banko | 128/276 |
| 4,020,847 | 5/1977 | Clark, III | 128/305 |
| 4,168,698 | 9/1979 | Ostergard | 128/751 |
| 4,174,715 | 11/1979 | Hasson | 128/321 |
| 4,178,810 | 12/1979 | Takahashi | 74/501 |
| 4,200,111 | 4/1980 | Harris | 128/751 |
| 4,282,884 | 8/1981 | Boebel | 128/751 |
| 4,326,530 | 4/1982 | Fleury, Jr. | 128/303 |
| 4,393,872 | 7/1983 | Reznik et al. | 604/151 |
| 4,427,014 | 1/1984 | Bel et al. | 128/751 |
| 4,461,305 | 7/1984 | Cibley | 128/754 |
| 4,493,320 | 1/1985 | Treat | 128/303 |
| 4,522,206 | 6/1985 | Whipple et al. | 128/312 |
| 4,574,803 | 3/1986 | Storz | 128/305 |
| 4,619,260 | 10/1986 | Magill et al. | |
| 4,620,547 | 11/1986 | Boebel | 128/754 |
| 4,644,951 | 2/1987 | Bays | 128/305 |
| 4,651,753 | 3/1987 | Lifton | 128/751 |
| 4,662,371 | 5/1987 | Whipple et al. | 128/312 |
| 4,682,606 | 7/1987 | De Caprio | 128/754 |
| 4,693,257 | 9/1987 | Markham | 128/752 |
| 4,721,116 | 1/1988 | Schintgen et al. | 128/751 |
| 4,733,662 | 3/1988 | DeSatnick et al. | 128/305 |
| 4,735,215 | 4/1988 | Goto et al. | 128/754 |
| 4,763,668 | 8/1988 | Macek et al. | 128/751 |
| 4,817,630 | 4/1989 | Schintgen et al. | 128/751 |
| 4,830,002 | 5/1989 | Semm | 128/321 |
| 4,836,205 | 6/1989 | Barrett | |
| 4,867,156 | 9/1989 | Stack et al. | 128/305 |
| 4,881,550 | 11/1989 | Kothe | 128/752 |
| 4,887,612 | 12/1989 | Esser et al. | 128/751 |
| 4,903,709 | 2/1990 | Skimmer | 128/754 |
| 4,909,782 | 3/1990 | Semm et al. | 606/171 |
| 4,926,877 | 5/1990 | Bookwalter | 128/754 |
| 4,953,559 | 9/1990 | Salerno | 128/751 |
| 4,971,067 | 11/1990 | Bolduc et al. | 128/751 |
| 4,976,269 | 12/1990 | Mehl | 128/754 |
| 4,986,825 | 1/1991 | Bays et al. | 604/22 |
| 5,026,379 | 6/1991 | Yoon | 606/141 |
| 5,052,402 | 10/1991 | Bencini et al. | 128/751 |
| 5,074,311 | 12/1991 | Hasson | 128/754 |
| 5,082,000 | 1/1992 | Picha et al. | 128/751 |
| 5,085,658 | 2/1992 | Meyer | 606/46 |
| 5,098,440 | 3/1992 | Hillstead | 606/108 |
| 5,111,828 | 5/1992 | Kornberg et al. | 128/754 |
| 5,133,727 | 7/1992 | Bales et al. | 606/170 |
| 5,147,378 | 9/1992 | Markham | 606/206 |
| 5,148,813 | 9/1992 | Bucalo | 128/754 |
| 5,172,700 | 12/1992 | Bencini et al. | 128/751 |
| 5,195,533 | 3/1993 | Chin et al. | 128/754 |
| 5,197,484 | 3/1993 | Kornberg et al. | 128/754 |
| 5,211,655 | 5/1993 | Hasson | 606/205 |
| 5,217,458 | 6/1993 | Parins | 606/48 |
| 5,217,468 | 6/1993 | Clement | 606/127 |
| 5,224,488 | 7/1993 | Neuffer | 128/751 |
| 5,228,451 | 7/1993 | Bales et al. | 128/751 |
| 5,234,000 | 8/1993 | Hakky et al. | 128/754 |
| 5,238,002 | 8/1993 | Devlin et al. | 128/751 |
| 5,251,641 | 10/1993 | Xavier | 128/754 |
| 5,267,572 | 12/1993 | Bucalo | 128/754 |
| 5,281,230 | 1/1994 | Heidmueller | 606/127 |
| 5,331,971 | 7/1994 | Bales et al. | 128/749 |
| 5,334,198 | 8/1994 | Hart et al. | 606/52 |
| 5,342,390 | 8/1994 | Slater et al. | 128/749 |
| 5,375,608 | 12/1994 | Tiefenbrun et al. | 128/754 |
| 5,383,471 | 1/1995 | Funnel | 128/751 |
| 5,394,887 | 3/1995 | Haaga | 128/749 |

MULTIPLE BIOPSY SAMPLING DEVICE

This is a continuation of application Ser. No. 08/597,878, filed Feb. 7, 1996, now abandoned, which is a continuation of application 08/124,272 filed Sep. 20, 1993, now abandoned.

FIELD OF THE INVENTION

This invention relates to taking samples of tissue from the body for biopsy analysis.

BACKGROUND OF THE INVENTION

Tissue samples can be examined in a laboratory to determine the presence of a pathological disorder (e.g. malignancy). Often, the samples must be obtained from deep within the body using a medical sampling instrument. It is usually best to obtain several samples around the location where the disorder is suspected so that the presence and progress of disease, if any, can be accurately determined. The samples must be catalogued according to the location from which each sample is taken and the integrity of the samples must be maintained for the subsequent laboratory analysis.

SUMMARY OF THE INVENTION

In one aspect, the invention relates to an instrument for obtaining tissue samples from a site deep within the body. The instrument has an elongated proximal portion that is constructed to follow a long, torturous path to the site and has a distal end constructed to sever and remove a tissue sample from the body, including tissue specimens, polyps or the like. The improvement includes that the instrument is constructed to take multiple biopsy samples without being withdrawn from the body. The instrument includes a tissue sample retractor. The retractor is axially movable between an extended tissue-engaging position and a retracted position. There is an open passage into which the retractor moves when moving from the extended to the retracted position. The retractor has a distal end portion constructed to engage tissue and apply axial transporting force thereto while moving from the extended to the retracted position. The retractor is constructed to be advanced and retracted repeatedly to accumulate a series of samples in the instrument.

In another aspect, the invention features an instrument for obtaining endoscopic tissue samples. The instrument is sized and constructed to pass through the working channel of an endoscope to take samples including tissue specimens, polyps or the like, under endoscopic guidance. The device has a distal end constructed to sever and remove a tissue sample from the body. The improvement includes the instrument constructed to take multiple biopsy samples without being withdrawn from the endoscope. The instrument includes a tissue sample storage device with a tissue-penetrating element having a distal barb formation. The barb formation is arranged to facilitate entry into tissue during advancement against the tissue and to resist distal dislodgment of the sample after the barb has penetrated the tissue.

In another aspect, the invention features an instrument for obtaining endoscopic tissue samples. The instrument is sized and constructed to pass through the working channel of an endoscope to take samples including tissue specimens, polyps or the like, under endoscopic guidance. The instrument has a distal end constructed to sever and remove a tissue sample from the body. The improvement includes the instrument constructed to take multiple biopsy samples without being withdrawn from the endoscope. The instrument includes a tissue sample storage device, wherein the storage device comprises a helical cork-screw-like projection constructed to be rotated to enter tissue.

In another aspect, the invention features an instrument for obtaining endoscopic tissue samples. The instrument is sized and constructed to pass through the working channel of an endoscope to take samples including tissue specimens, polyps or the like, under endoscopic guidance. The instrument has a distal end constructed to sever and remove a tissue sample from the body. The improvement includes the instrument constructed to take multiple biopsy samples without being withdrawn from the endoscope. The instrument includes a tissue sample storage device. The sample storage device includes an elongated tissue penetrating element of length sufficient to accommodate at least three samples and constructed to enable a specimen to be slidably advanced progressively thereover away from a severing device of the instrument as additional samples are taken as a result of pressure transmitted through the previously taken samples during the spearing action on the next sample, thereby to prepare the instrument to take further samples.

In another aspect, the invention features an instrument for obtaining endoscopic tissue samples. The instrument is sized and constructed to pass through the working channel of an endoscope to take samples including tissue specimens, polyps or the like, under endoscopic guidance. The instrument has a distal end constructed to sever and remove a tissue sample from the body. The improvement includes the instrument constructed to take multiple biopsy samples without being withdrawn from the endoscope. The instrument includes a severing device with at least one pivotable jaw. The jaw has a pair of pivotable jaw support portions lying close to respective sides of a supporting structure, there being an open space for multiple tissue sample storage between the support portions.

Embodiments of the invention may include combinations of the features above and also have one or more of the following features. The instrument has a severing device including at least one pivotable jaw. The jaw has a pair of pivotable jaw support portions lying close to respective sides of a supporting structure. There is an open space for multiple tissue sample storage between the support portions. The retractor is a tissue-penetrating element. The tissue-penetrating element has a barb formation arranged to facilitate entry into tissue during advancement against the tissue and to apply axial transporting force to the tissue during retraction movement. The tissue-penetrating element is constructed and arranged to penetrate a mid-portion of the sample of tissue being taken. The penetrating element is elongated and constructed to spear and securely store thereupon, in stacked relationship, a series of tissue samples in the order in which the samples have been taken. The element is sufficiently long to store a series on the order of three, e.g., five or more tissue samples. Multiple barbs are disposed along the length of the element, constructed to enable a specimen to be advanced progressively over the barbs as additional samples are taken as a result of pressure transmitted through the previously taken samples during the spearing action on the next sample. The retractor is a helical cork-screw-like projection constructed to be rotated to enter tissue and constructed to move axially to retract the tissue sample. The cork-screw-like projection is sufficiently long to store thereupon a series on the order of five or more tissue samples, in the sequence in which the samples have been taken. Helical threads extend along the length of the projection along which previously-taken samples advance when, upon further rotation, additional samples are taken. The retractor is constructed to extend along the side of a sample being severed and has a laterally-extending dragger formation constructed to engage the sample and apply proximally-directed transporting force thereto. The retractor is constructed and arranged relative to the open passage to drag successive severed samples into the passage and stack them therein in the order in which the samples have been taken. The severing device includes at least one pivotable jaw and one stationary jaw. The retractor is of generally tongue form and during severing action lies along the stationary jaw. The retractor is of wire form and has a distal hook formation constructed to apply proximally-directed transporting force to the sample. The retractor is an axially displaceable grasper constructed to grasp the tissue sample by pinching action for transport of the sample. The grasper includes tong-like grippers constructed to grasp and transport a tissue sample. The grippers are closed upon a sample by axial movement of an actuating tube slidingly disposed over structure connected to the grippers. The movable retractor is constructed to draw the severed sample into the passage away from a severing device of the instrument to prepare the instrument to take further samples. The severing device has at least one actuatable cutting jaw. The jaw is supported on the distal end of a tubular structure. An internal portion of the structure provides space for tissue sample storage. The severing device includes opposed actuatable cutting jaws. The jaws are constructed to be closed upon a sample by axial movement of an actuating tube slidingly disposed over supporting arms of the jaws. The jaw is pivotably supported by supporting structure and control means extend along the instrument for pivoting the jaw. The instrument includes a severing device in the form of a snare loop projectable from the instrument over tissue to be removed. The instrument is sized and constructed to pass through the working channel of an endoscope to take multiple samples under endoscopic guidance without being withdrawn from the endoscope.

Embodiments may also include one or more of the following features. The tissue penetrating element, upon completion of taking of the samples, is constructed to be detached from the instrument and be sent to the pathology laboratory with the samples intact upon the element in the order in which the specimens were taken. The element is constructed and arranged, upon completion of use and withdrawal from the body, to extend distally beyond sample severing mechanism of the instrument to enable the multiple samples to be removed therefrom.

Embodiments may also include one or more of the following features. The instrument has a distal supporting tube, a distal extremity of the tube constructed to form a fixed jaw, and the pivotable jaw has support arms lying close to respective sides of the tube and being pivotably mounted with respect thereto. The arms lie on the exterior of the tube. The arms lie in the interior of and closely adjacent to respective sides of the interior wall of the tube. A respective short pin-formation pivotably mounts each arm to the tube. A through-axle extend across the interior of the tube, upon which the arms are mounted, open space being provided adjacent the axle for storage of the tissue samples.

Other features and advantages follow.

BRIEF DESCRIPTION OF THE DRAWING

We first briefly describe the drawings.

DESCRIPTION OF THE PREFERRED EMBODIMENTS

Figure 1:
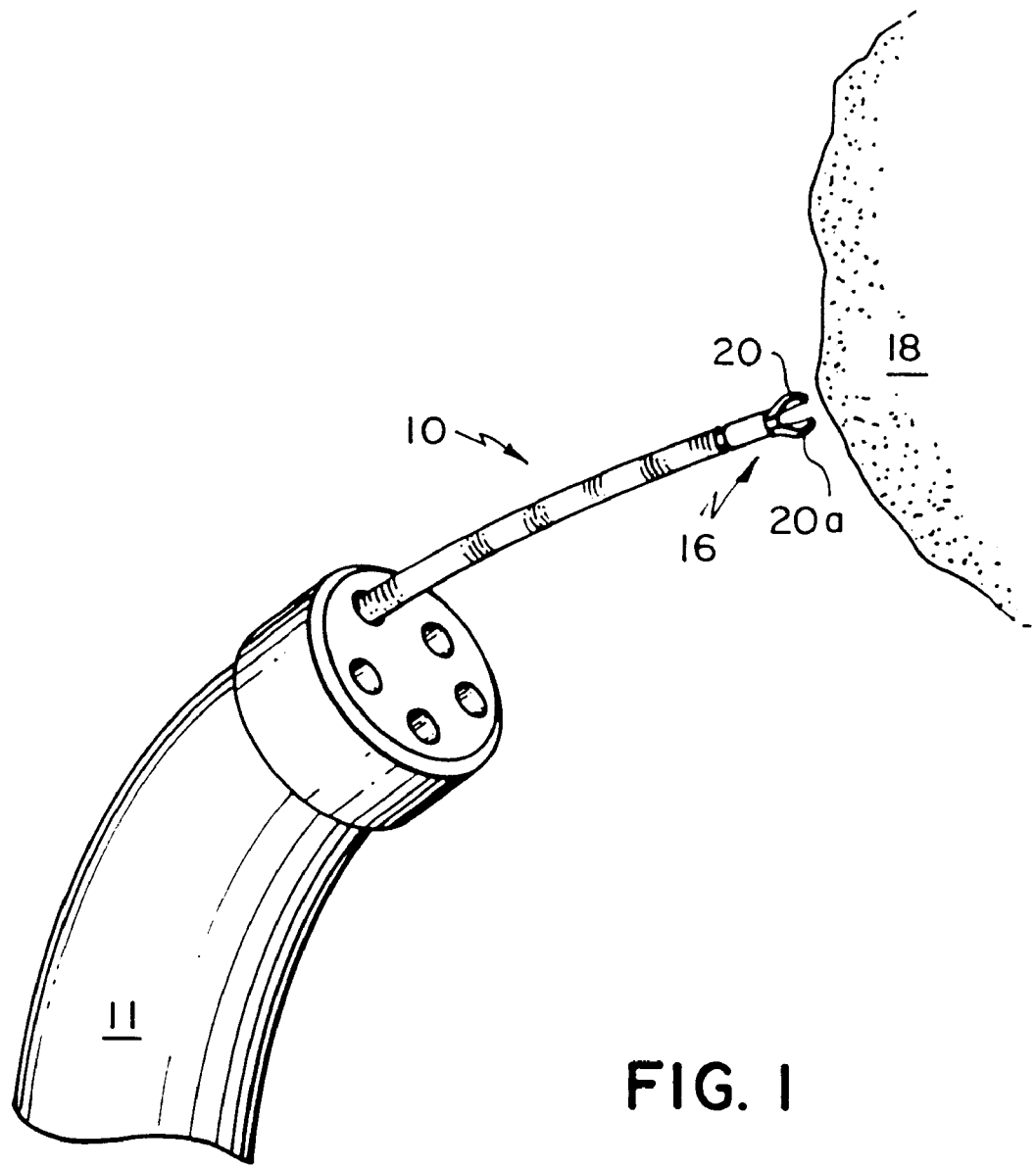
FIG. 1 is a perspective view of an embodiment of the invention being delivered into the body through an endoscope.

Referring to FIG. 1, the device 10 for multiple biopsy sampling may be delivered into the body through the channel of an endoscope device 11 (e.g., gastroscope, sigmoidoscope, or colonoscope). The endoscope device typically has a length of about 100–250 cm and a channel diameter of 2.0–3.8 mm, typically about 2.8 mm. A distal sampling portion 16 is extended from the endoscope for cutting and storing a sample of tissue from a body surface 18 of a patient (e.g. from a surface in the gastrointestinal tract, bronchial tract, urinary tract, reproductive organs, cardiac tissue, or the like). The device has a diameter of preferably around 1.8–2.4 mm, typically about 2.3 mm or less and is of sufficient flexibility so it passes easily though the channel when the endoscope follows a tortuous body passageway. The endoscope includes other lumens for water, air, suction, and viewing. Devices according to the invention can be adapted to be introduced to sites deep within the body by other means. For example, a device can be configured with a lumen so that it can be advanced over a guidewire, e.g., in vascular applications. The device may be passed through an introducer or guiding catheter in, e.g., cardiac applications. The sampling and storage arrangements may be useful in open surgery applications.

Figure 2:
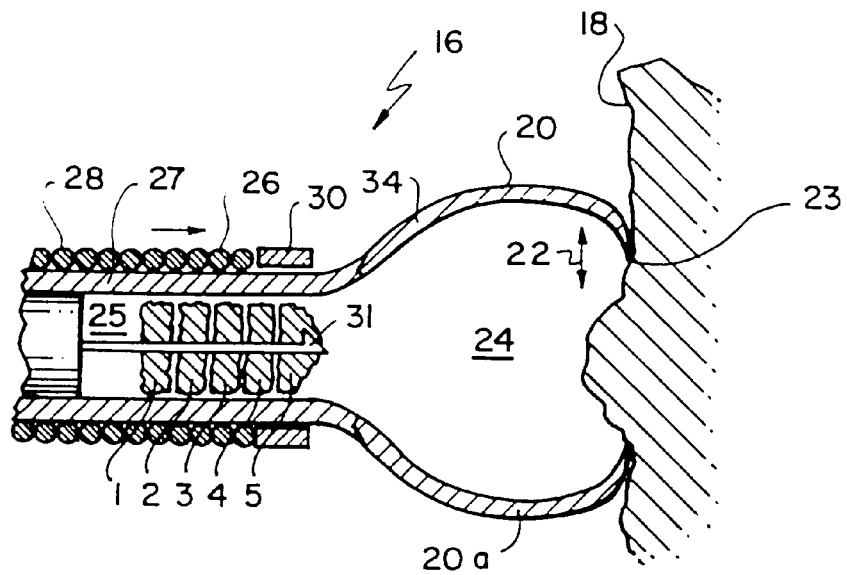
FIGS. 2–2c are cross sectional views that illustrate the structure and use of an embodiment of the invention.
Figure 2A:
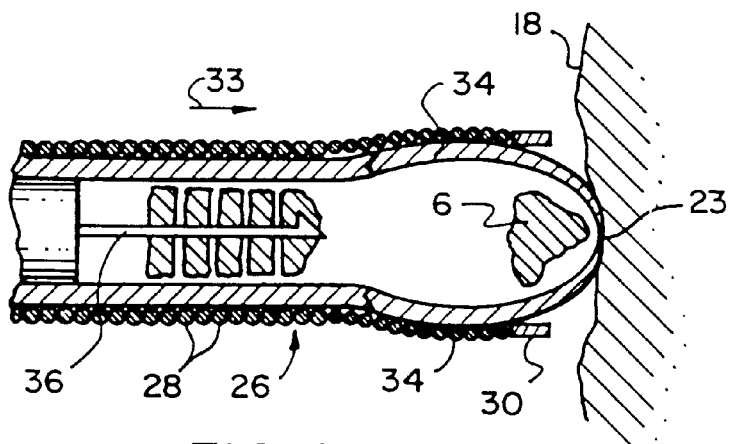
Figure 2B:
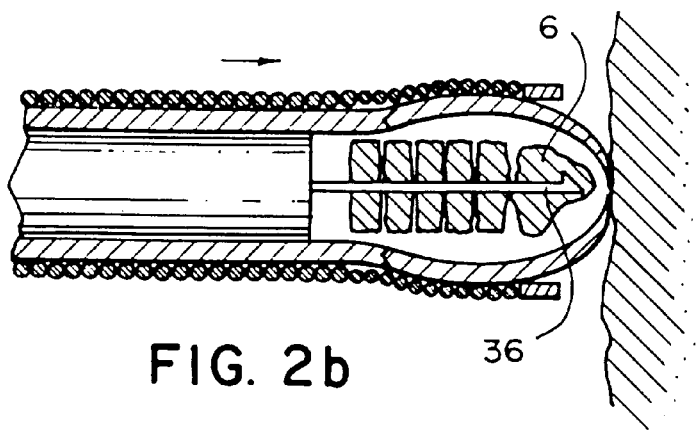
Figure 2C:
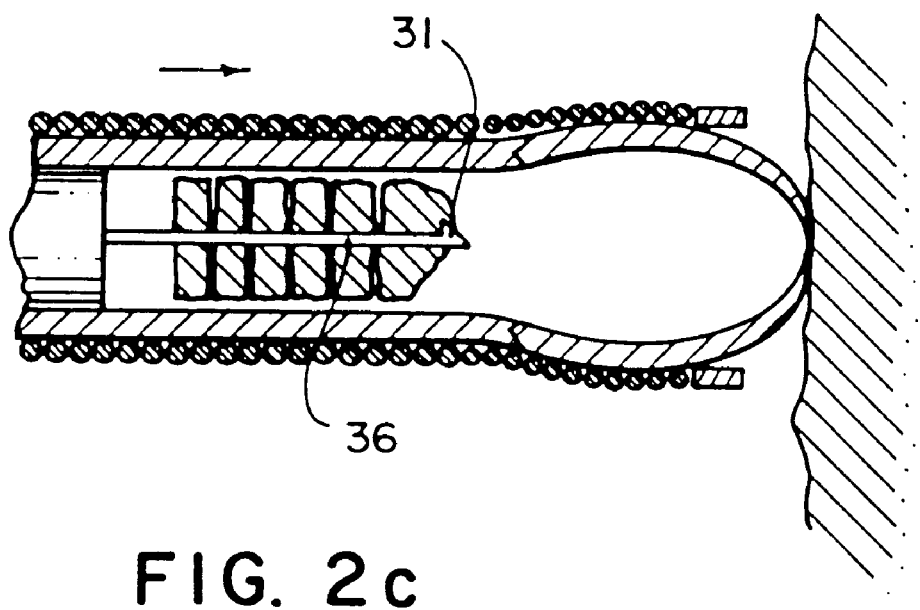

Referring to FIGS. 2–2c, in an embodiment, the sampling portion 16 includes a pair of jaw members 20, 20a which are movable with respect to each other (arrow 22) between an open and closed position. The outer edge 23 of the jaw members includes a sharp cutting edge for cutting a sample of tissue from the body surface 18. Jaw members 20, 20a are formed of an elastic material, such as an elastic stainless steel, nitinol or the like, and are biased outwardly so the jaws are open in the relaxed configuration. The jaws encompass a space 24 in which a sample is contained after it is cut from the surface 18.

The space 24 communicates with an open throat region 25, just proximal of the jaws, where successive prior samples 1, 2, 3, 4 and 5 are stored, while the next sample, sample 6, is taken. The samples are stored in the order in which they taken by use of a retractor 36, which in this embodiment is a spear-form element that pierces the samples through their centers. As will be discussed in more detail below, the retractor can be moved axially into the space 25 to retreive a sample cut by the jaws by piercing it, then withdrawn proximally to store the samples in the throat.

The throat 25 and jaws 20, 20a, may be defined by a tubular member 27 that has been modified (e.g. slit longitudinally and worked) at its distal end to form jaws 20, 20a or the throat may be defined by a tube of a different material, to which the jaws are attached. There may be two jaw members, as shown, or there may be more than two jaw elements that fit together when the jaws are closed. The jaws may have sides to completely enclose the space 24 when the jaws are closed or the jaws may be open, like a clipper, such that only the cutting edges at the distal end of the jaws meet when closed. In use, with the jaws biased open, the device is urged against the tissue at a location where a sample is to be taken, as shown in FIG. 2.

Referring particularly to FIG. 2a, the jaws are closed by an axially movable, concentric sheath member 26. The sheath member, formed of a helical wire coil 28 for most of its length for increased flexibility, includes at its most distal end a short, stiff bearing member 30. By a suitable mechanical control located outside the body, the sheath is moved axially distally (arrow 33) to cause the bearing member 30 to bear on the outside portions 34 of the jaws 20, 20a to collapse them into a closed position so the cutting edge 23 cuts or edulses sample 6 from the body surface 18 of the patient.

Referring particularly to FIG. 2b, the elongated spear-form retractor 36 is movable along its axis into the space 24 encompassed by the jaws for piercing the next sample, sample 6. With the jaws closed, the sample 6 is pushed against the interior of the distal portions of the jaws and onto the retractor. The pressure against sample 6 is transferred to sample 5 and through the other samples, thus displacing previous samples 1–5 axially proximally along the body of the retractor.

Referring particularly to FIG. 2c, the spear-form retractor 36 is then withdrawn axially to store samples 1–6 in the open throat 25, as illustrated. The tip of the retractor is pointed to allow samples to be pierced but also includes a barb 31 that prevents the sample from slipping off during retraction. The spear-form element grasps and indexes successive samples 1–6 cut by the jaws in the order in which they were taken. The procedure above can be repeated so additional samples can be taken without removing the device from the endoscope.

Other Embodiments

Figure 3:
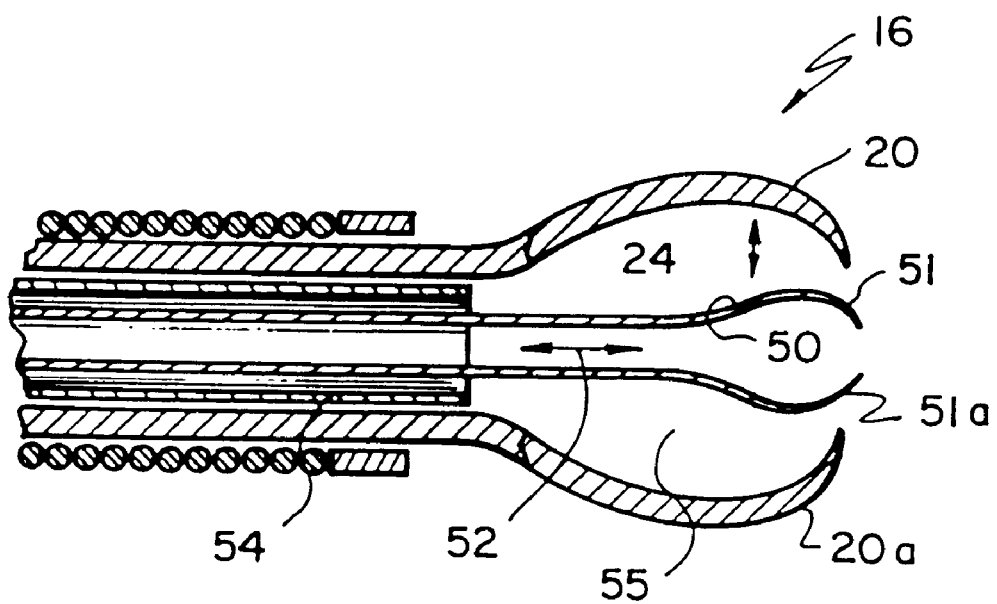
FIG. 3 is a cross sectional view of another embodiment of the invention.

Referring to FIG. 3, another embodiment of the invention as shown. In this case, the retractor is a forceps member 50, with jaws 51, 51a much smaller than the cutting jaws 20, 20a, so the retractor can be moved axially (arrow 52) in to the space 24 to grasp a sample and pull it back into the throat for storage. The jaws of the forceps member 50 may be biased in the open position, and closed by distal axial extension of an outer concentric sheath 54, like the closure of the jaws 20, 20a with sheath 26. A spear element (not shown) may be provided within the throat of the forceps 50, to hold multiple samples in the throat 55, proximal of the jaws 51,51a.

Figure 4:
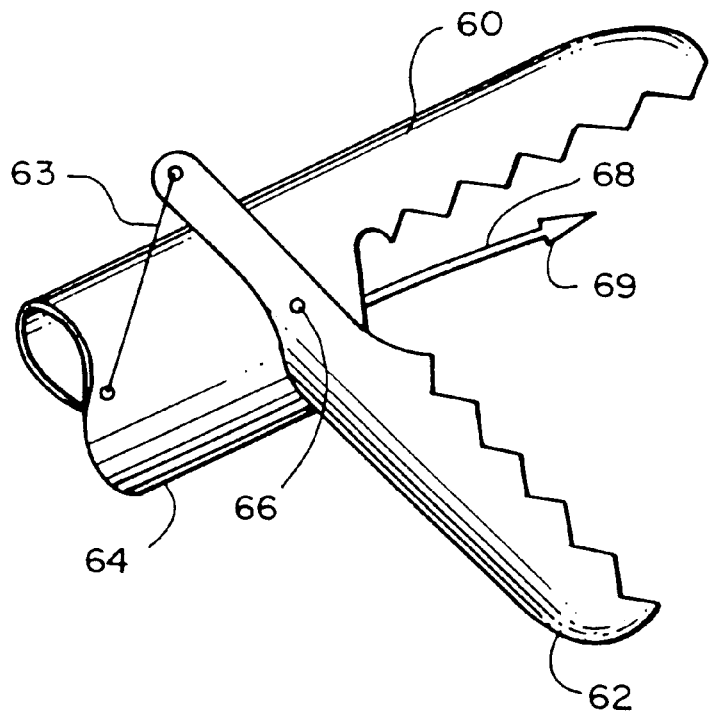
FIGS. 4–4f illustrate the structure and use of another embodiment of the invention.
Figure 4A:
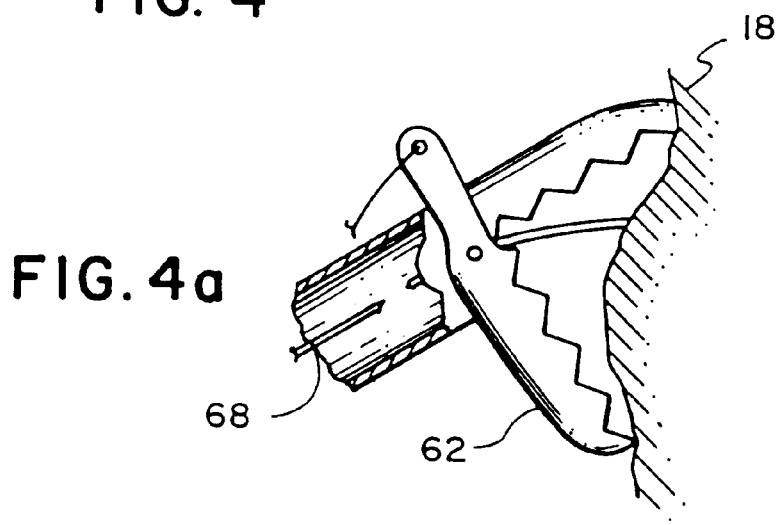
Figure 4B:
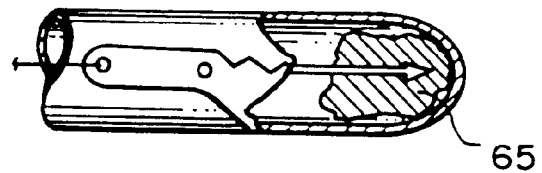
Figure 4C:
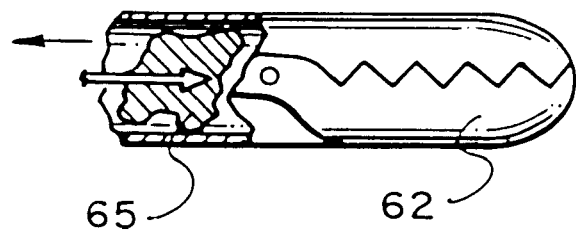
Figure 4D:
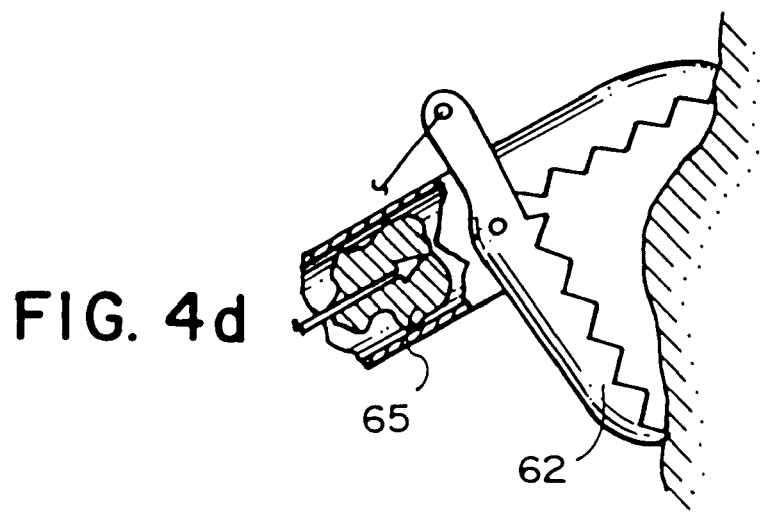
Figure 4E:
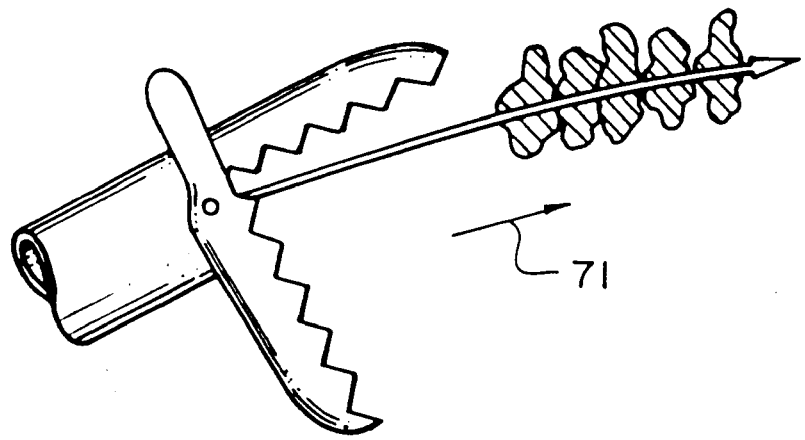
Figure 4F:
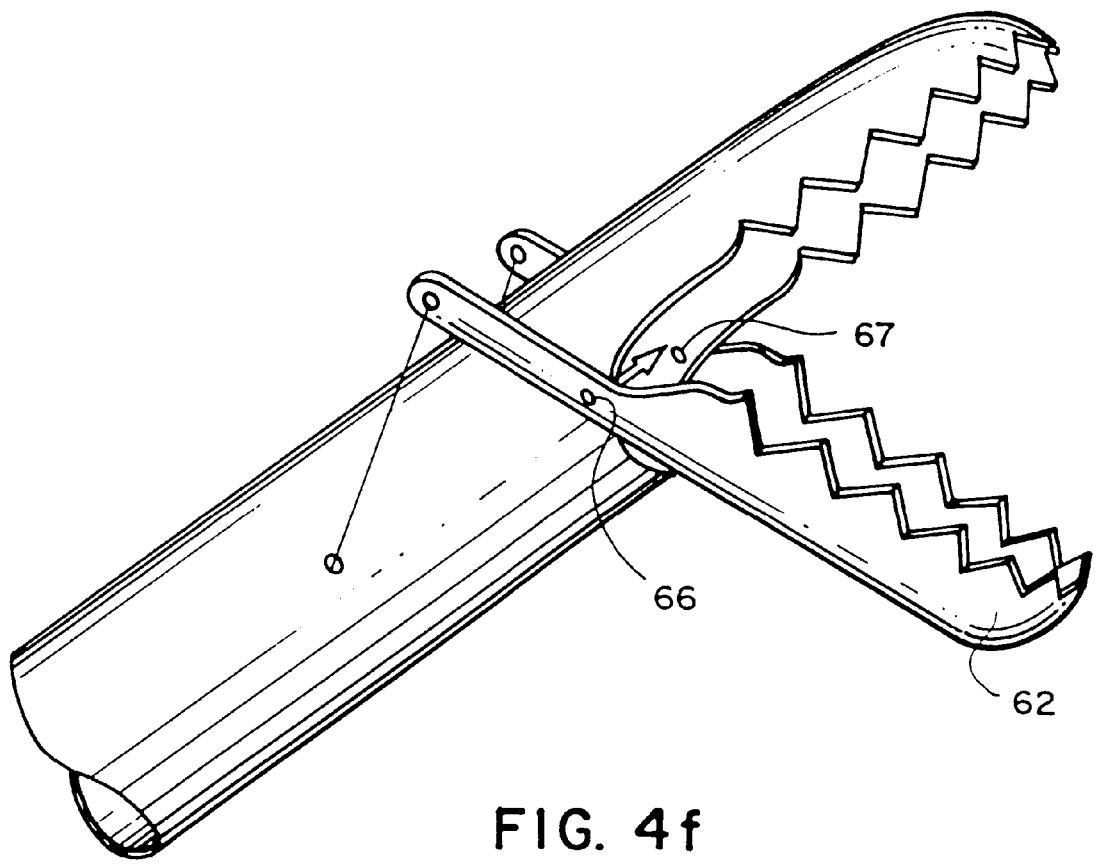

Referring to FIGS. 4–4f, another embodiment is shown. In this embodiment, a sampling forceps includes a stationary jaw 60 and a movable jaw 62. The movable jaw 62 is attached to the body 64 of the device at two hinge points 66, 67 and actuated between the open and closed position by pull wires 63. Referring particularly to FIG. 4f, a perspective view, the jaw 62 is hinged at opposite sides of the body 64 to provide the open throat area for storage of successive samples. The jaws may be hinged on either the outside of the body, as shown, or inside of the body. A movable or stationary retractor 68, with a barb or undercut 69, is used to anchor the device in tissue and hold samples after cutting.

Referring particularly to FIG. 4a, in use, the jaw 62 is opened and the retractor advanced into tissue 18. (The retractor can as well be advanced after the sample is cut as shown in FIGS. 2 et seq.) Previous samples are moved axially proximally along the retractor. Referring to FIG. 4b, using pull wire 63, the jaw 62 is closed and a tissue sample 65 is cut and captured by the jaws. The retractor is advanced forward axially to firmly hold the tissue. Referring to FIG. 4c, the retractor is then drawn axially proximally so that the tissue is located in the throat behind the jaws. Referring to FIG. 4d, the jaws are opened and the spear is re-advanced to take the next sample. Referring to FIG. 4e, to remove the multiple samples, after the device has been removed from the body, the jaws are opened and the spear moved axially distally (arrow 71) beyond the jaws where the samples can be easily accessed. The samples can but need not be removed from the spear. Rather, the end of the retractor carrying the samples can be detached at a location proximal of the samples (by cutting or by a reusable attachment mechanism) and the samples, still indexed on the spear according to the order they were taken, sent to the lab.

In alternate embodiments, the retractor is stationary and of extended length running from the throat region to the space within the jaws. In embodiments, the spear can be withdrawn proximally the full length of the device to remove it and access the samples while leaving the rest of the device in an endoscope.

Figure 5:
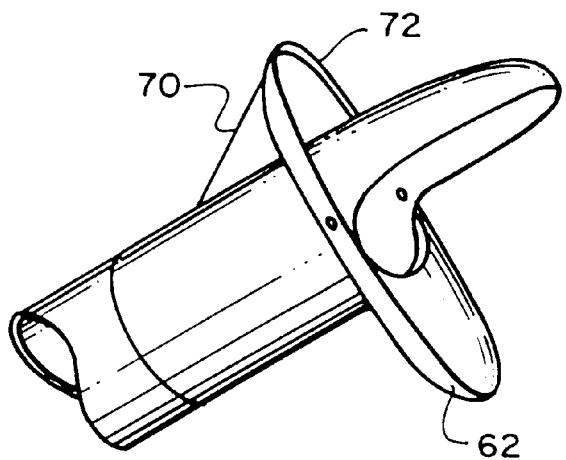
FIGS. 5–5a are perspective and top views, respectively, that illustrate another embodiment of the invention.
Figure 5A:
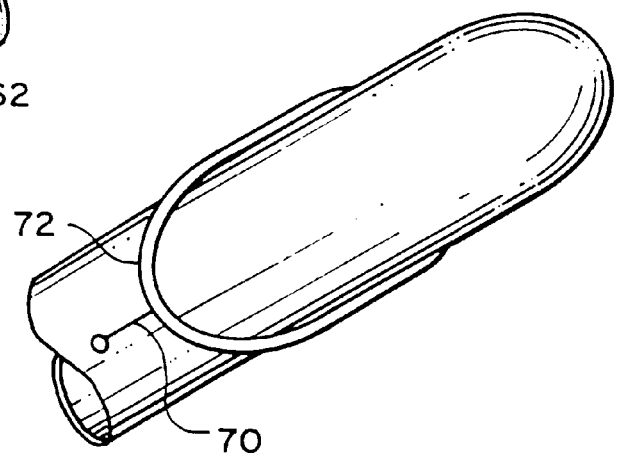

Referring to FIGS. 5 and 5a (top view), the jaw 62 may be operated by a single pull wire 70, attached centrally to a common pivot arm 72.

Figure 6:
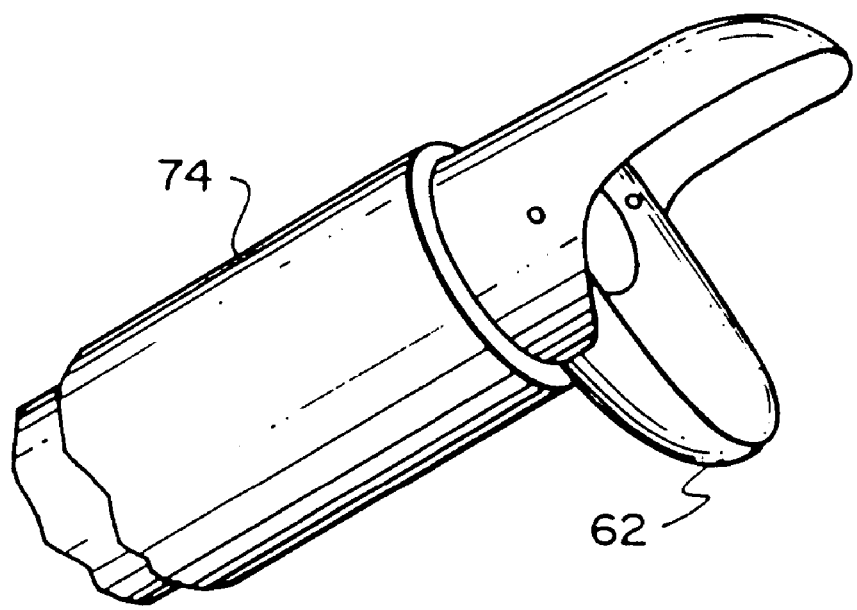
FIGS. 6–6a illustrate another embodiment of the invention.
Figure 6A:
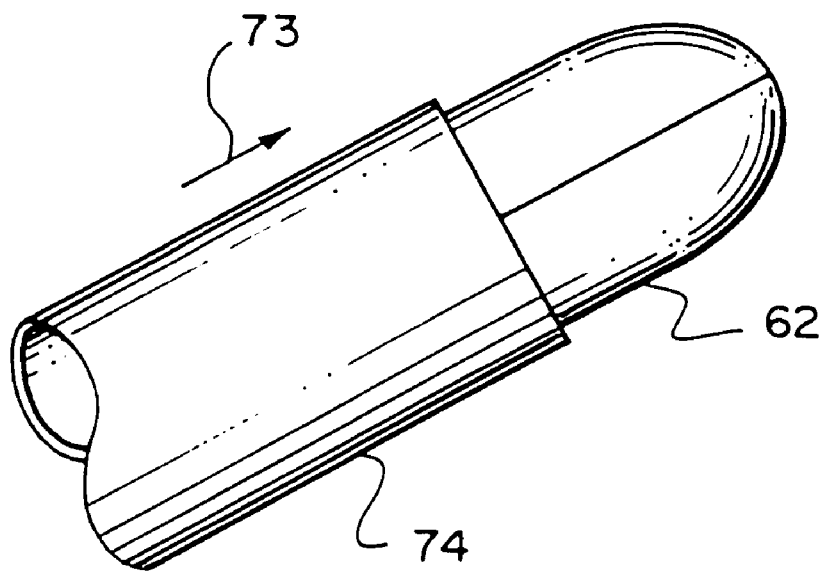

Referring to FIGS. 6–6a, the jaw 62 may be closed using a coaxial sheath 74, which is slid forward (arrow 73, FIG. 6a). The jaw 62 may be biased open using a spring at the pivot points or pulled open using a pull wire.

Figure 7:
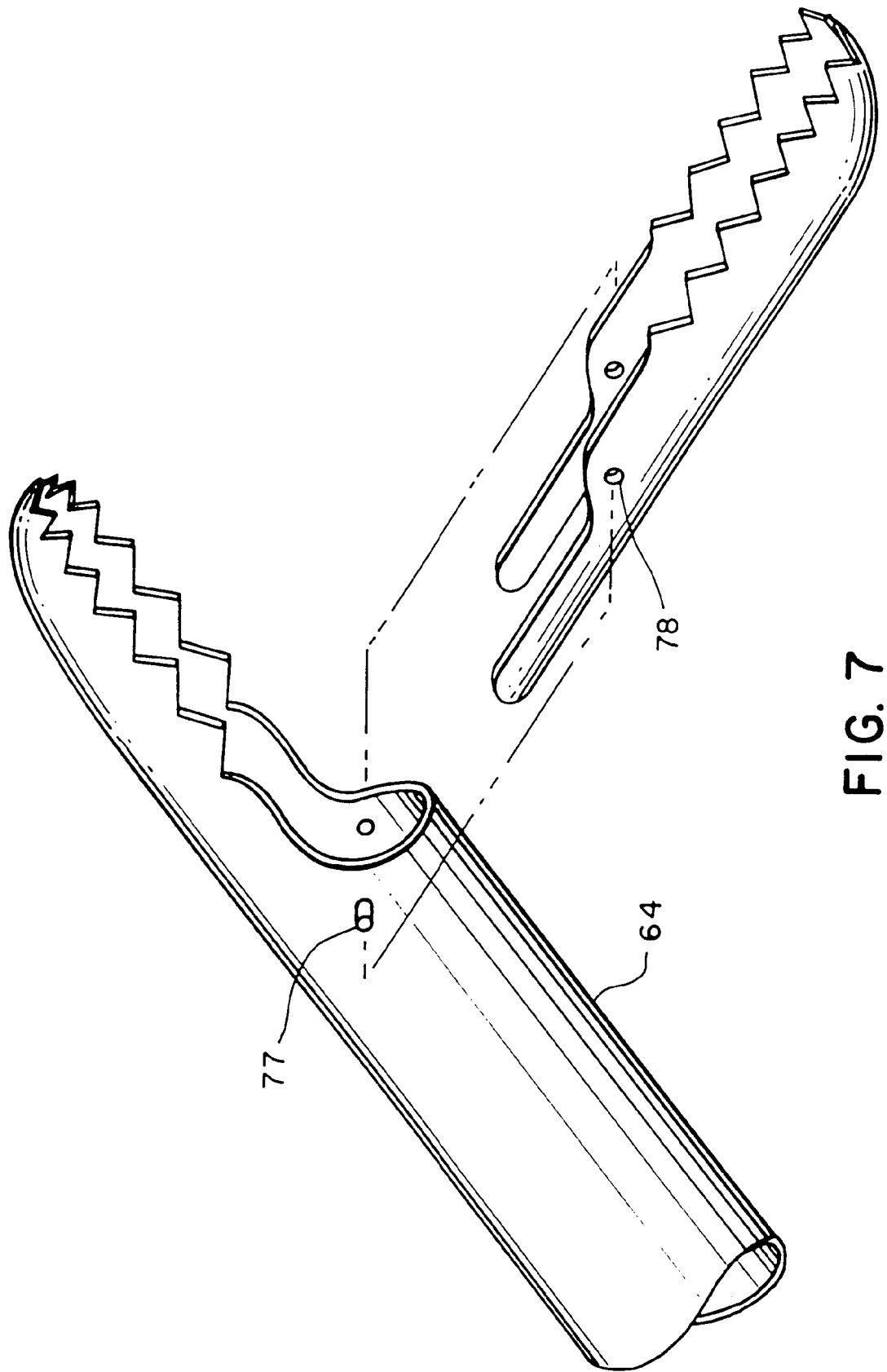
FIGS. 7–7c and 8 are assembly views that illustrate hinge arrangements for a moveable jaw according to the invention.
Figure 7A:
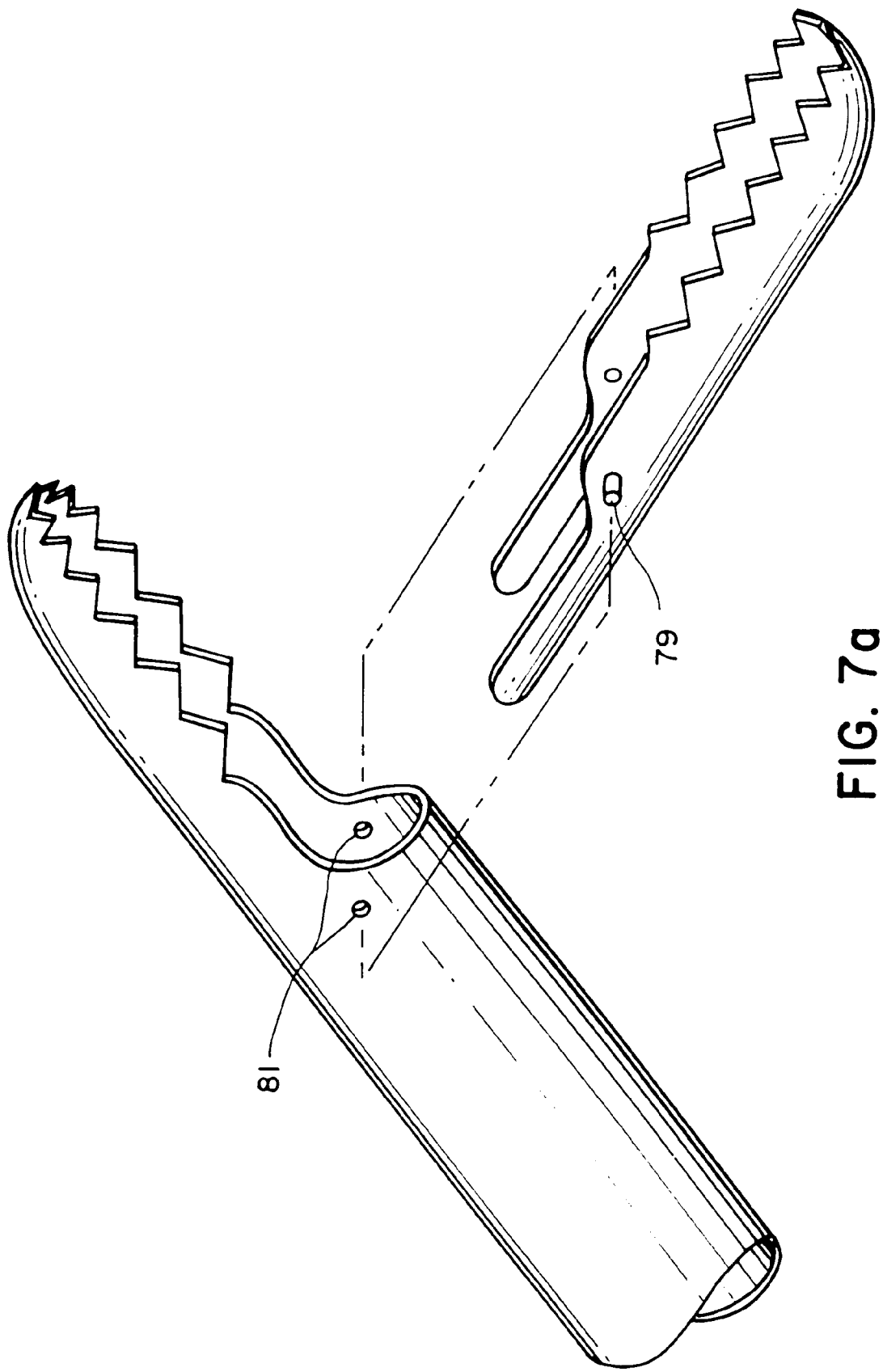
Figure 7B:
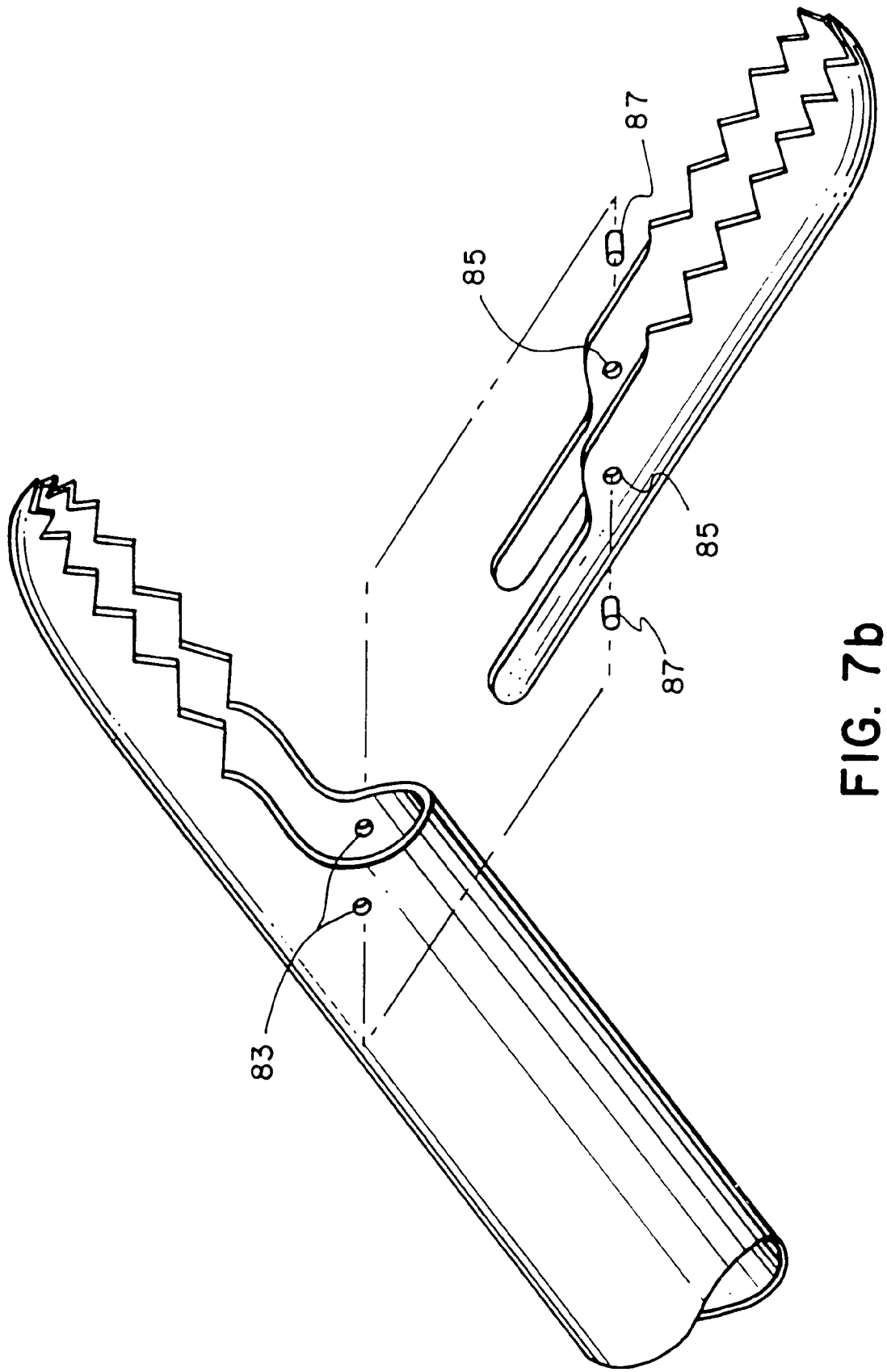
Figure 7C:
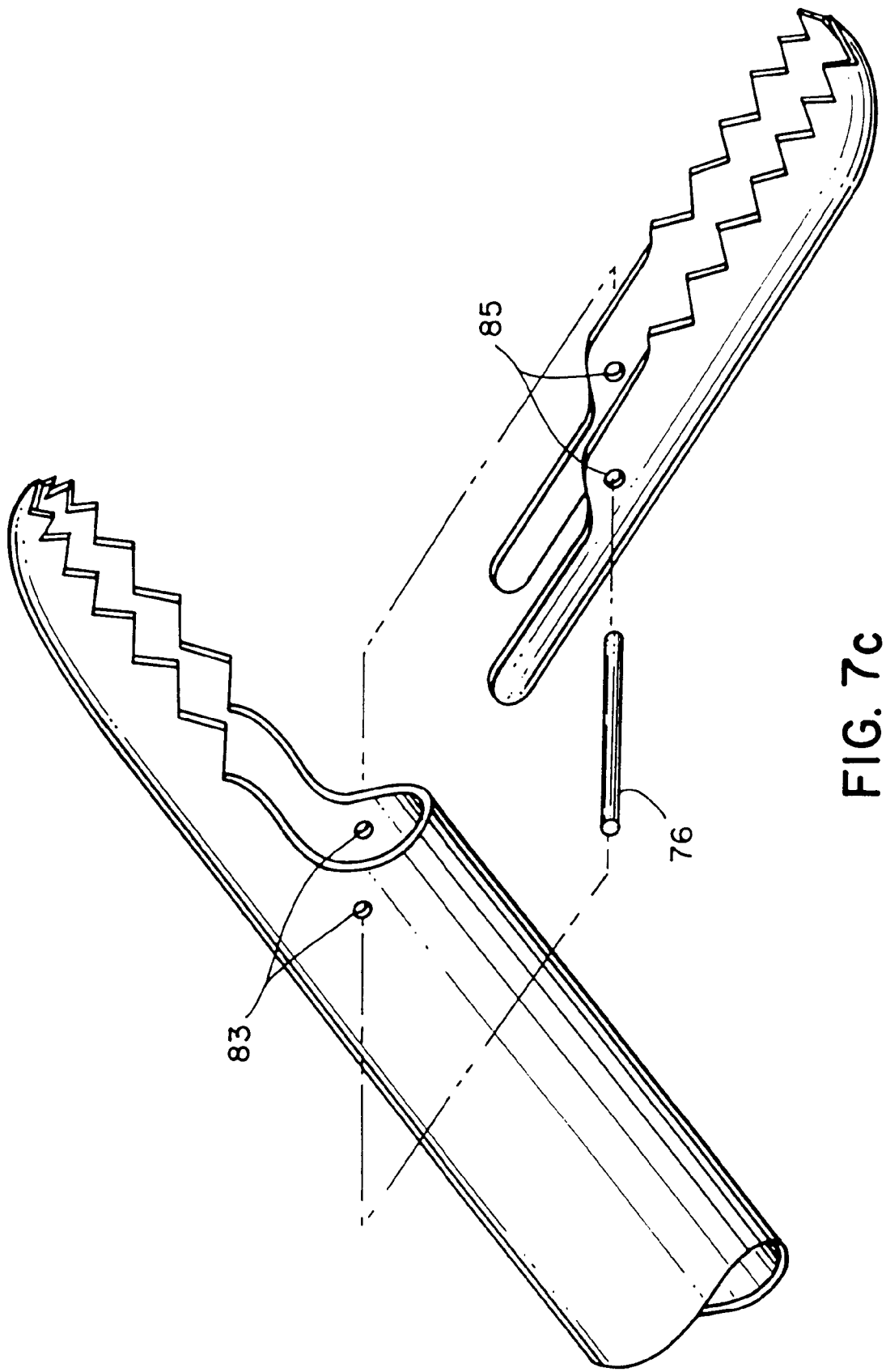

Referring to FIGS. 7–7c, the jaw 62 may be attached to the body of the device using separate pins at each pivot point. Pins 77 may be integral with the body of the device, to protrude into a hole 78 in the jaw (FIG. 7) or a pin 79 may protrude from the jaw into a hole 81 in the body (FIG. 7a). One pivot point may have one construction and the other pivot point the other construction. Both the jaws and body may include holes 83,85 which are adapted for separate pins 87 (FIG. 7b) or a single pin 76 may pass through the body of the device (FIG. 7c). In the latter embodiment, the retractor can pass to one or the other side of the pin. The pin 76 could also be modified to include rotatable extensions, which like a paddle wheel, could draw samples from the jaws and place them in the throat for storage.

Figure 8:
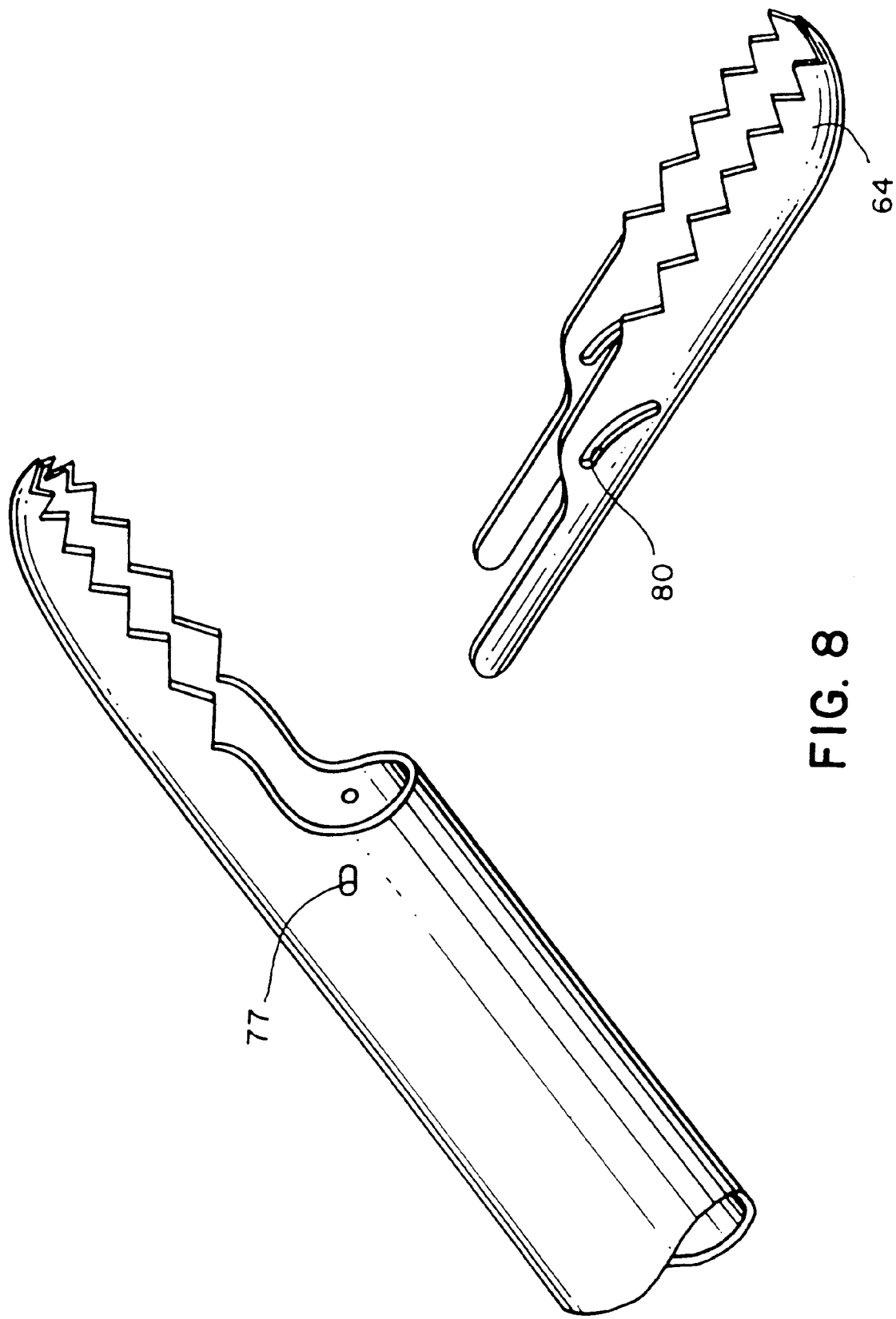

Referring to FIG. 8, an elongated slot 80 or cam configuration may be provided at the pivot point for opening the movable jaw 64 wider and increasing cutting force and action. In use, the jaw is opened and slid distally to grab tissue. Then the jaw is closed by rotation about the pivot point while drawing the jaw proximally along the slot.

Figure 9:
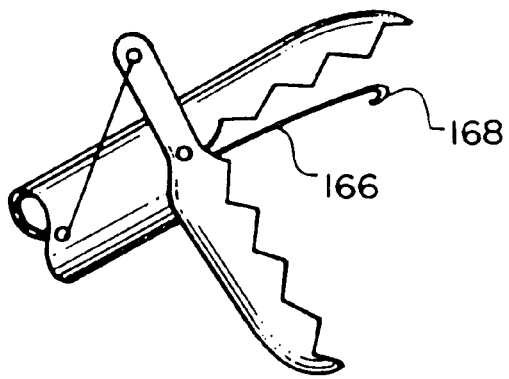
FIGS. 9–9c and 10–10a illustrate tissue sample retractor arrangements according to the invention.
Figure 9A:
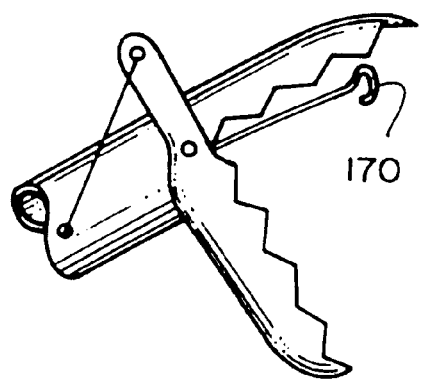
Figure 9B:
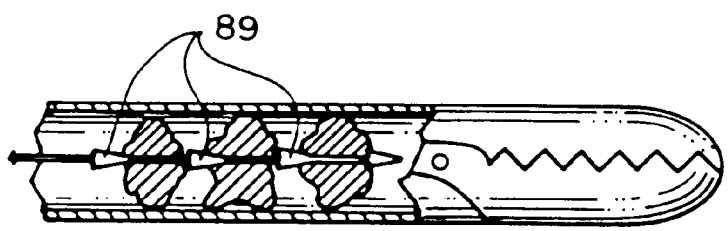
Figure 9C:
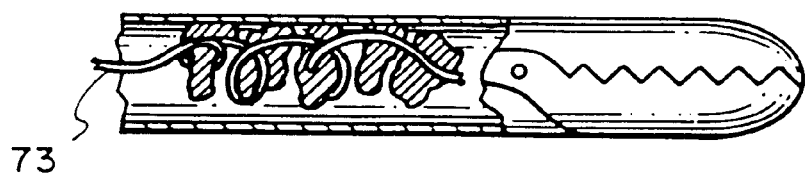

Referring to FIGS. 9–9c, various additional retractor embodiments are illustrated. Referring particularly to FIG. 9, the retractor may be a preformed wire member 166 with a hook end 168 which is used to snare or trap the tissue so that it can be withdrawn into the device. Referring to FIG. 9a, the retractor may be a loop end device 170. By rotating the body of the retractor about its axis, the loop can be rotated to catch tissue. The sample can then be withdrawn into the throat by withdrawing the retractor axially. Referring to FIG. 9b, the body of the member can be provided with a number of small, axially separated barbs 89 that separate and retain adjacent samples. Referring to FIG. 9c, the retractor may be a rotatable spiral-form cork-screw member 73 (shown symbolically) that collects and stores the samples along the spiral surface by rotation of the member about its own axis. The cork-screw-like projection can be rotated to enter a tissue sample and then withdrawn axially into the the throat. Helical threads extend along the projection on which previous samples advance when, upon further rotation, additional samples are taken.

Figure 10:
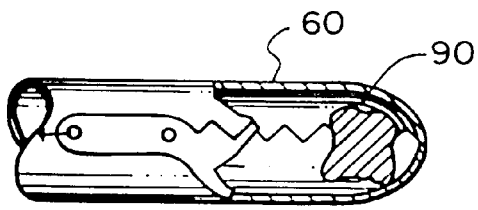
Figure 10A:
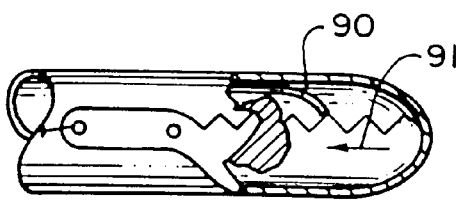

Referring to FIGS. 10–10a in another embodiment, an axially movable tongue 90 is provided. The tongue is shaped to conform to the inner contour of one of the jaws, typically the stationary jaw 60. After the jaws have cut the sample, the tongue can be drawn proximally (arrow 91) to drag the sample into the throat for storage (FIG. 10a).

In other embodiments, the distal end of the retractor may be straight, without an undercut or barb, e.g. the tip may be rounded. The retactor may include a reduced diameter section proximal of the tip. The member may be formed of metal, plastic, composite or combinations thereof. Preferably, the member has considerable length compared to its width for storing multiple samples.

Figure 11:
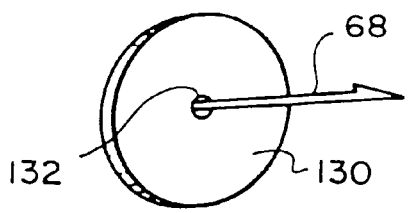
FIGS. 11–11c illustrate positioning of retractors according to the invention.
Figure 11A:
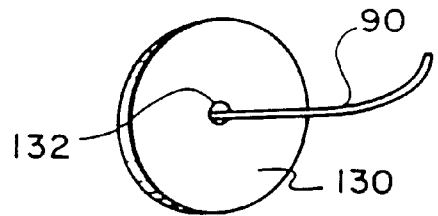
Figure 11B:
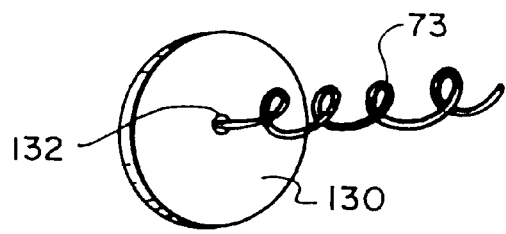
Figure 11C:
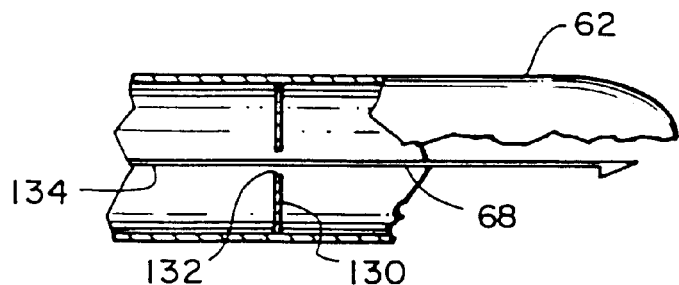

Referring to FIGS. 11–11c, in cases where the retractor is to be centered or otherwise carefully positioned with respect to the axis of the device body, a positioning plate 130 may be located in the body just proximal of the throat. The positioning plate has an aperture 132. The retractor passes through the aperture distally. Proximally, a wire 134, integral or attached to the retractor, extends to the proximal end of the device to control axial movement of the retractor.

Figure 12:
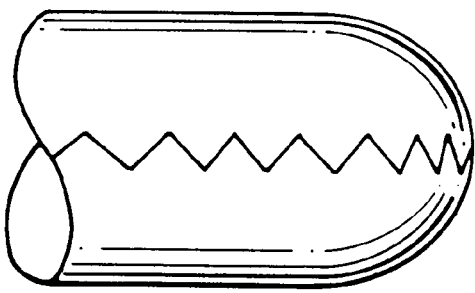
FIGS. 12–12d illustrate various jaw configurations for use with forceps embodiments of the invention.
Figure 12A:
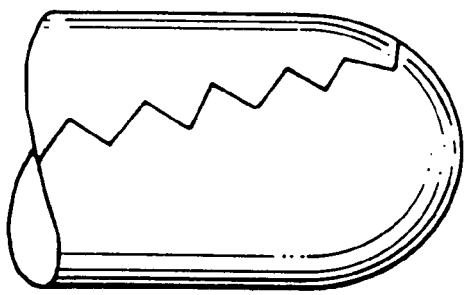
Figure 12B:
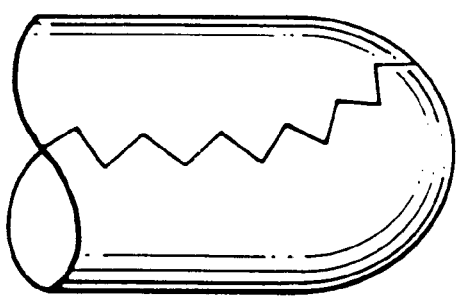
Figure 12C:
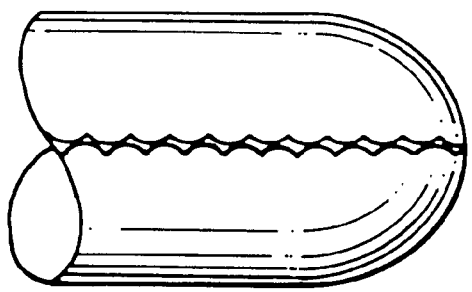
Figure 12D:
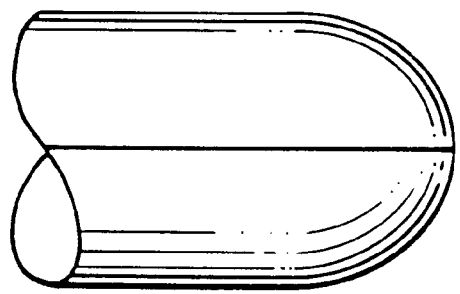

Referring to FIGS. 12–12d, the jaws of the device may be of a variety of designs for particular applications. The jaws may have a straight plane through the center (FIG. 12). The jaws may be angled with respect to the center (FIG. 12a). The jaws may follow a curved plane through the center (FIG. 12b). The cutting edges of the jaws may be jagged (FIG. 12a), serrated (FIG. 12c) or razor-edged (FIG. 12d). The jaws can be provided with a heating means, such as an electrical current, to assist in cutting.

Figure 13:
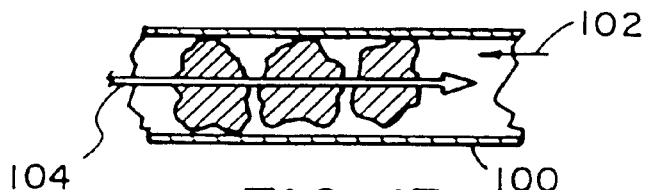
FIG. 13 illustrates another embodiment of the invention.

Referring to FIG. 13, another embodiment is shown. The device includes an open tubular member 100 capable of providing suction in the direction (arrow 102) of the proximal end of the device. A grasping spear-form member 104 stacks and stores successive samples as they are drawn into the tubular member by the suction. Means other than forceps may be used to cut the sample from the body, e.g., suction alone.

Figure 14:
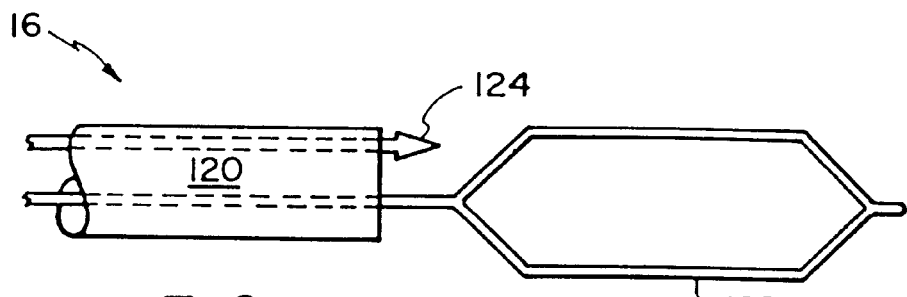
FIGS. 14–14d illustrate the structure and use of yet another embodiment of the invention.
Figure 14A:
Figure 14B:
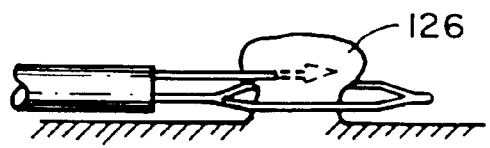
Figure 14C:
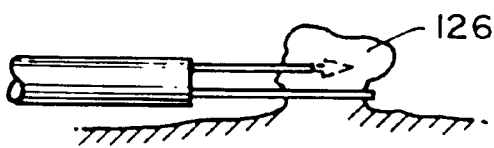
Figure 14D:
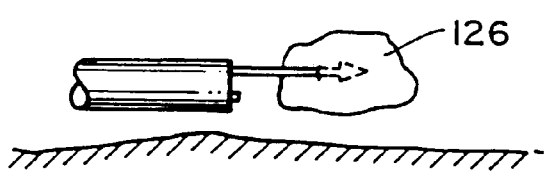

Referring to FIGS. 14–14d, another embodiment is shown. The device includes a delivery catheter 120, suitable for passage through an endoscope. The cather may have a single, or preferably, multiple lumens. The catheter 120 carries, in one of its lumens, a polypectomy snare-type wire loop 122 and, in another lumen, a tissue retention device such as a retractor 124 with a barb 125.

Referring to FIG. 14a, in use, the snare wire loop is positioned around a polyp 126 attached to the wall of the alimentary tract. Referring to FIG. 14b, the spear-form element is advanced into the polyp until its barb 125 is completely within the polyp. Referring to FIG. 14c, the polyp is severed from the wall by actuating the snare wire loop. Referring to FIG. 14d, the snare wire loop is withdrawn into the catheter. Referring to FIG. 14d, the sample is then held by the spear-form member. Additional samples can be taken and stored on the spear-form member by repeating the above steps.

The grasping members shown in each of the embodiments above can be used in each of the other embodiments above. In general, suction can be used to assist operation of any of the embodiments above.

A system for taking multiple biopsy samples is taught in Chu "Instruments for Collecting Multiple Biopsy Specimens", U.S. Ser. No. 062,671, filed May 17, 1993, the entire contents of which is hereby incorporated by reference.

Still other embodiments are within the following claims.

What is claimed is:

1. In an instrument for obtaining tissue samples from a site deep within the body, the instrument having an elongated proximal portion that is constructed to follow a long, torturous path to said site, and having a distal end constructed to sever and remove a tissue sample from the body, including tissue specimens, polyps or the like, the improvement wherein said instrument is constructed to take multiple biopsy samples without being withdrawn from the body, said instrument including an actuatable severing member for severing said sample and a separately actuatable tissue sample retractor, said retractor being axially movable between an extended tissue-engaging position and a retracted position, there being an open passage into which said retractor moves when moving from said extended to said retracted position, said retractor having a distal end portion constructed to engage tissue and apply axial transporting force thereto while moving from said extended to said retracted position, said retractor constructed and arranged to be advanced and retracted repeatedly to accumulate a series of samples in said instrument without withdrawing the instrument from the body.

2. The instrument of claim 1 having a severing device comprising at least one pivotable jaw, the jaw having a pair of pivotable jaw support portions lying close to respective sides of a supporting structure, there being an open space for multiple tissue sample storage between said support portions.

3. The instrument of claim 1 wherein said retractor comprises a tissue-penetrating element.

4. The instrument of claim 3 wherein said tissue-penetrating element has a barb formation arranged to facilitate entry into tissue during advancement against the tissue and to apply axial transporting force to said tissue during retraction movement.

5. The instrument of claim 3 wherein said tissue penetrating element is constructed and arranged to penetrate a mid-portion of the sample of tissue being taken.

6. The instrument of claim 5 wherein said penetrating element is elongated and constructed to spear and securely store thereupon, in stacked relationship, a series of tissue samples in the order in which said samples have been taken.

7. The instrument of claim 6 wherein said element is sufficiently long to store a series on the order of three or more tissue samples.

8. The instrument of claim 6 wherein multiple barbs are disposed along the length of said element, constructed to enable a specimen to be advanced progressively over said barbs as additional samples are taken as a result of pressure transmitted through the previously taken samples during the spearing action on the next sample.

9. The instrument of claim 3 wherein said retractor comprises a helical cork-screw-like projection constructed to be rotated to enter tissue and constructed to move axially to retract the tissue sample.

10. The instrument of claim 9 wherein said cork-screw-like projection is sufficiently long to store thereupon a series on the order of five or more tissue samples, in the sequence in which said samples have been taken.

11. The instrument of claim 10 in which helical threads extend along the length of said projection along which previously-taken samples advance when, upon further rotation, additional samples are taken.

12. The instrument of claim 1 wherein said retractor is constructed to extend along the side of a sample being severed and having a laterally-extending dragger formation constructed to engage the sample and apply proximally-directed transporting force thereto.

13. The instrument of claim 12 wherein said retractor is constructed and arranged relative to said open passage to drag successive severed samples into the passage and stack them therein in the order in which said samples have been taken.

14. The instrument of claim 12 having a severing device comprising at least one pivotable jaw and one stationary jaw, said retractor being of generally tongue form and during severing action lying along said stationary jaw.

15. The instrument of claim 12 where said retractor is of wire form and has a distal hook formation constructed to apply proximally-directed transporting force to said sample.

16. The instrument of claim 1 wherein said retractor comprises an axially displaceable grasper constructed to grasp said tissue sample by pinching action for transport of said sample.

17. The instrument of claim 16 wherein said grasper comprises tong-like grippers constructed to grasp and transport a tissue sample.

18. The instrument of claim 17 wherein said grippers are closed upon a sample by axial movement of an actuating tube slidingly disposed over structure connected to said grippers.

19. The instrument of claim 1 in which said movable retractor is constructed to draw the severed sample into said passage away from a severing device of the instrument to prepare the instrument to take further samples.

20. The instrument of claim 19 wherein said severing device comprises at least one actuatable cutting jaw.

21. The instrument of claim 2 or 20 wherein said jaw is supported on the distal end of a tubular structure, an internal portion of said structure providing space for tissue sample storage.

22. The instrument of claim 20 wherein said severing device comprises opposed actuatable cutting jaws.

23. The instrument of claim 22 wherein said jaws are constructed to be closed upon a sample by axial movement of an actuating tube slidingly disposed over supporting arms of said jaws.

24. The instrument of claim 20 wherein said jaw is pivotably supported by supporting structure and control means extend along the instrument for pivoting said jaw.

25. The instrument of claim 1 comprising a severing device in the form of a snare loop projectable from the instrument over tissue to be removed.

26. The instrument of claim 1 wherein said instrument is sized and constructed to pass through the working channel of an endoscope to take multiple samples under endoscopic guidance without being withdrawn from the endoscope.

27. In an instrument for obtaining tissue samples, the instrument sized and constructed to pass through the working channel of an endoscope to take samples including tissue specimens, polyps or the like, under endoscopic guidance and having a distal end constructed to sever and remove a tissue sample from the body, the improvement wherein said instrument is constructed to take multiple biopsy samples without being withdrawn from the endoscope, said instrument including a severing member for severing said sample and a separate tissue sample storage device, said tissue sample storage device comprising a tissue-penetrating element having a distal barb formation, said barb formation constructed and arranged to facilitate entry into tissue and to resist distal dislodgment of said sample after said barb has penetrated said tissue to accumulate a series of samples without withdrawing the instrument from the endoscope.

28. The instrument of claim 27 wherein said penetrating element is elongated and constructed to spear and store thereupon, in stacked relationship, a series of tissue samples in the order in which said samples have been taken.

29. The instrument of claim 27 wherein multiple barbs are disposed along the length of said element, constructed to enable a specimen to be advanced progressively over said barbs as additional samples are taken as a result of pressure transmitted through the previously taken samples during the spearing action on the next sample.

30. In an instrument for obtaining tissue samples, the instrument sized and constructed to pass through the working channel of an endoscope to take samples including tissue specimens, polyps or the like, under endoscopic guidance and having a distal end constructed to sever and remove a tissue sample from the body, the improvement wherein said instrument is constructed to take multiple biopsy samples without being withdrawn from the endoscope, said instrument including a tissue sample storage device, said sample storage device comprising an elongated tissue penetrating element of length sufficient to accommodate at least three samples and constructed to spear a sample and enable the sample to be slidably advanced progressively thereover away from a separate severing device of the instrument as additional samples are taken as a result of pressure transmitted through the previously taken samples during the spearing action on the next sample, thereby to prepare the instrument to take further samples without withdrawing the instrument from the endoscope.

31. The instrument of claim 30 wherein said tissue penetrating element, upon completion of taking of said samples, is constructed to be detached from the instrument and be sent to the pathology laboratory with said samples intact upon said element in the order in which said specimens were taken.

32. The instrument of claim 30 wherein said element is constructed and arranged, upon completion of use and withdrawal from the body, to extend distally beyond sample severing mechanism of the instrument to enable said multiple samples to be removed therefrom.

* * * * *